US005665581A

United States Patent [19]
Chen et al.

[11] Patent Number: 5,665,581
[45] Date of Patent: Sep. 9, 1997

[54] ATTENUATION OF FUNGAL VIRULENCE BY SYNTHETIC INFECTIOUS MYCOVIRUS TRANSCRIPTS

[75] Inventors: Baoshan Chen, Bloomfield; Gil Ho Choi, Nutley; Donald Lee Nuss, Passaic, all of N.J.

[73] Assignee: Hoffmann-La Roche Inc., Nutley, N.J.

[21] Appl. No.: 253,451

[22] Filed: Jun. 3, 1994

[51] Int. Cl.$^6$ ................................................. C12N 13/00
[52] U.S. Cl. ........................... 435/173.6; 435/172.1; 435/254.11; 435/256.8; 935/52
[58] Field of Search ............... 47/DIG. 11; 800/DIG. 8; 424/93 A, 93 B, 93 C, 93 Q; 435/172.1, 172.2, 172.3, 254.1, 254.11; 536/23.72

[56] References Cited

PUBLICATIONS

GC Ainsworth (1971) Dictionary of the Fungi p. 140.
GH Choi et al (1992) Science 257:800–803.
RA Jaynes et al (1980) Phytopathology 70:453–456.
BI Hillman et al (1990) Phytopathology 80:950–956.
AL Shigo (1984) Ann Rev Phytopathiol 22:189–214.
Turchetti et al., "Mixed inoculum for the biological control of chestnut blight", Bulletin OEPP/EPPO, 18:67–72 (1988).
Turchetti and Maresi, "Inocultion trials with hypovirulent strains of Cryphonectria parasitica", Eur. J. For. Path., 21:65–70 (1991).
Anagnostakis, "Improved chestnut tree condition maintained in two Connecticut plots after treatments with hypovirulent strains of the chestnut blight fungus", Forest Science 36:113–124 (1990).
Shapira et al., "Virus–like genetic organization and expression strategy for a double–stranded RNA genetic element associated with biological control of chestnut blight", EMBO J. 10:731–739 (1991).
Choi and Nuss, "A viral gene confers hypovirulence-associated traits to the chestnut blight fungus", EMBO J. 11:473–477 (1992).

Choi et al., "Cotranslational autoproteolysis involved in gene expression from a double–stranded RNA genetic element associated with hypovirulence of the chestnut blight fungus", PNAS (USA) 88:1167–1171 (1991).
Choi et al., "The autocatalytic protease p29 encoded by a hypovirulence–associated virus of the chestnut blight fungus resembles the potyvirus–encoded protease HC–Pro", Virology 183:747–752 (1991).
Shapira and Nuss, "Gene expression by a hypovirulence-associated virus of the chestnut blight fungus involved tow papain–like protease activities", J. Biolog. Chem., 266:19419–19425 (1991).
Koonin et al., "Evidence for common ancestry of a chestnut blight hypovirulence–associated double–stranded RNA and a group of positive–strand RNA plant viruses", PNAS (USA) 88:10647–10651 (1991).
Nuss et al., "Significance of dsRNA genetic elements in plant pathogenic fungi", Annu. Rev. Phytopathol. 28:37–58 (1990).
Shapira et al., "The contribution of defective RNAs to the complexity of viral–encoded double–stranded RNA populations present in hypovirulent strains of the chestnut blight fungus Cryphonectria parasitica", The EMBO J. 10:741–746 (1991).
Van Alfen, "Biology and potential for disease control of hypovirulence of Endothia parasitica", Annu. Rev. Phytopathol 20:349–362 (1982).

(List continued on next page.)

Primary Examiner—Bruce R. Campbell
Attorney, Agent, or Firm—George W. Johnston; Dennis P. Tramaloni; Bruce A. Pokras

[57] ABSTRACT

This invention is directed to naturally virulent fungi which have cells transfected with the coding strand of a mycovirus RNA and which have reduced ability to cause disease in plants, and to compositions and methods of treatment of fungal disease with these fungi.

2 Claims, 6 Drawing Sheets

PUBLICATIONS

Rae et al., "Characterization of double-stranded RNA genetic elements associated with biological control of chestnut blight: organization of terminal domains and identification of gene products", EMBO J. 8:657–663 (1989).

Hillman et al., "Hypovirulence-associated suppression of host functions in Cryphonectria parasitica can be partially relieved by high light intensity", Phytopathology 80:950–956 (1990).

Boyer and Haenni, "Infectious transcripts and cDNA clones of RNA viruses", Virology 198:415–426 (1994).

Morris and Dodds, "Isolation and analysis of double-stranded RNA from virus-infected plant and fungal tissue", Phytopathology, 69:854–858 (1979).

Rogers et al., "A mitochondrial target for double-stranded RNA in diseased isolates of the fungus that causes Dutch elm disease", Nature 329:558–560 (1987).

Hammar et al., "Association of double-stranded RNA with low virulence in an isolate of Leucostoma persoonii", Phytopthology 79:568–572 (1989).

Bottacin et al., "Characterization of dsRNA in Chalara elegans and effects on growth an virulence", Phytopathology 84:303–312 (1994).

Bandy and Tavantzis, "Effect of hypovirulent Rhizoctonia solani on Rhizoctonia disease, growth, and development of potato plants", American Potato J. 67:189–199 (1990).

Chen et al., "Mitotic stability and nuclear inheritance of integrated viral cDNA in engineered hypovirulent strains of the chestnut blight fungus", EMBO J. 12:2991–2998 (1993).

Grente and Berthelay-Sauret, "Biological control of chestnut blight in France", Proceedings of the American Chestnut Symposium, pp. 30–34, eds. MacDonald et al., University of W. Virgina Press, Morgantown (1978).

Jaynes and Elliston, "Control of Endothia parasitica cankers on American chestnut sprouts with hypovirulent strains", Proceedings of the American Chestnut Symposium, pp. 110–114, eds. MacDonald et al., University of W. Virginia Press, Morgantown (1978).

Chen et al., "Attenuation of fungal virulence by synthetic infectious hypovirus transcripts", Science 264:1762–1764 (194).

Craven et al., "Papain-like protease p29 as a symptom determinant encoded by a hypovirulence-associated virus of the chestnut blight fungus", J. of Virology 67:6513–6521 (1993).

Chen et al., "cDNA-derived hypovirus RNA in transformed chestnut blight fungus is spliced and trimmed of vector nucleotides", Virology 202:441–448 (1994).

Websters Ninth New Collegiate Dictionary (1990) p. 1253.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:1:

TAATACGACT CACTATAG     18

ATTENUATION OF FUNGAL VIRULENCE BY SYNTHETIC INFECTIOUS MYCOVIRUS TRANSCRIPTS

BACKGROUND OF THE INVENTION

More than 100 fungal species have been reported to harbor viruses (mycoviruses), (K. W. Buck, *Fungal virology—an overview* (CRC Press, Boca Raton, Fla., 1985)). Mycovirus infections are persistent, non-transmissible by an extracellular route and generally non-symptomatic, (Buck, supra and R. B. Wickner, *FASEB* 3, 2257 (1989)). However, members of the genus *Hypovirus* cause profound phenotypic alterations, including virulence attenuation (hypovirulence), in their host, the chestnut blight fungus *Cryphonectria parasitica*. Hypoviruses can be transmitted intercellularly to compatible virulent strains of *C. parasitica* through fused hyphae (anastomoses), (Van Alfen et al., P. R. Day, *Science* 189, 890 (1975) and S. L. Anagnostakis, P. R. Day, *Phytopathology* 69, 1226 (1979)). Thus, the application of hypovirus-attenuated *C. parasitica* strains can, under appropriate conditions, reduce or control progression of this fungal disease (Anagnostakis, S. L. (1982). Science, 215–466–471; S. L. Anagnostakis (1990), Forest Science 36, 113–124; Grente, J. and S. Berthelay-Sauret, (1978), p. 30–34. in W. L MacDonald, F. C. Cech, J. Luchok and H. C. Smith (eds) Proceedings of American Chestnut Symposium. West Virginia University Press, Morgantown; (Murr.). (Bart. S. L. Anagnostakis, *Science* 215, 466 (1982)).

The prototypic hypovirus, isolate CHV1-713 from hypovirulent *C. parasitica* strain EP713, is found predominantly as unencapsidated double-stranded RNA (L-dsRNA) with an organization similar to a replicative intermediate of a positive strand RNA virus, (Shapira, et al. *EMBO J.* 10, 731 (1991)). Attempts to artificially transmit hypoviruses by introduction of viral dsRNA into virus-free fungal strains have been unsuccessful (N. K. Van Alfen, *Hypovirulence of Endothia (Cryphonectria) parasitica and Rhizoctonia solani*. (CRC Press, Boca Raton, Fla., 1986)). Applicants have discovered that a hypovirus infection can be established in pathogenic fungi by introducing a synthetic copy of the L-dsRNA coding strand into fungal cells, resulting in reduced virulence.

SUMMARY OF THE INVENTION

This invention is directed to a fungus which comprises a cell of a naturally virulent fungus causing disease in plants, said cell transfected with a coding strand of a mycovirus RNA which mycovirus RNA reduces the ability of said naturally virulent fungus to cause disease in plants, and said mycovirus RNA being transmissible by said cell to other cells of the same fungus. Included in this invention is a method for producing this fungus having reduced virulence.

Also part of this invention is a composition which comprises the above fungus and a carrier nontoxic to plants, where the fungus is present in the composition in sufficient amounts to treat fungal disease in plants when the composition is applied to a plant, and a method for treating fungal diseases in plants which comprises administering this composition to a plant infected with a naturally virulent infecting fungus in an amount sufficient to treat the fungal disease Caused by the infecting fungus.

A method for preventing fungal diseases in plants which comprises administering the composition to a plant in an amount sufficient to prevent infection of said plant with a naturally virulent fungus is also part of this invention.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

FIG. 3. Virulence assay of *E. gyrosa* on dormant stems of pin oak and red oak. The extent of tissue necrosis for representative lesions formed by uninfected (U) and hypovirus-infected (I) *E. gyrosa* on the two oak species is clearly seen after removing the overlying bark. Quantitative virulence data are presented in Table 1.

DETAILED DESCRIPTION

This invention is directed to a fungus which comprises a cell of a naturally virulent fungus causing disease in plants, said cell transfected with a coding strand of a mycovirus RNA which mycovirus RNA reduces the ability of said naturally virulent fungus to cause disease in plants, and said mycovirus RNA being transmissible by said cell to other cells of said fungus. In this invention, the term fungus includes a fungus composed of one cell or composed of multiple cells, and a fungal spheroplast. By means of this invention, plant disease caused by fungal infection can be controlled.

Naturally virulent fungi which cause diseases in plants (also known as plant pathogenic fungi) are well known in the art. Such fungi and their cells may be obtained for example from infected plants. Examples of such fungi are *Cryphonectria cubensis* and *Cryphonectria havanensis*, which cause disease in species of eucalyptus trees, and *Endothia gyrosa*, which causes disease in oak trees (Quercus) such as red oak and pin oak. Any such fungi may be a fungus of this invention.

Mycovirus RNA of this invention reduces virulence, virulence being the ability to cause disease. Mycovirus RNA occurs naturally in certain naturally virulent fungi, but not in others. When mycovirus RNA of this invention occurs in naturally virulent fungi which cause disease in plants, the ability of these fungi to cause disease in plants is accordingly reduced.

Mycovirus RNA is naturally found in double-stranded form, composed of a coding strand and a noncoding strand. Mycovirus RNA may be obtained by conventional methods from any fungus which contains a mycovirus (for examples of such fungi see Nuss and Koltin, Ann.Rev.Phytopathol. 28: 37–58 (1990)). Mycovirus RNA which reduces virulence in naturally virulent fungi is found, for example, in the following fungi: *Ophiostoma ulmi*, *Leucostama persoonii*, *Rhizoctonia solani*, *Chalara elegans* and *Cryphonectria parasitica*. Any other mycovirus RNA which reduces virulence in naturally virulent fungi may be used in this invention.

There is no method in the literature to transfect (by which is meant artificially insert or infect) double-stranded mycovirus RNA into fungi. As part of this invention, applicants have discovered that a single strand of mycovirus RNA which is the coding strand, can be transfected into fungi, specifically naturally virulent fungi which cause disease in plants. The mycovirus RNA replicates after transfection. The coding strand may be obtained from the double-stranded mycovirus by conventional methods. In addition, any mycovirus RNA which reduces natural virulence in fungi may be identified by a conventional assay. Mycovirus RNA obtained from a fungus may, by means of this invention, be inserted into and replicate in a cell of a selected naturally virulent fungus. Then, using the conventional assay appropriate to that naturally virulent fungus, reduction of virulence of the fungus by the mycovirus is determined. Examples of conventional assays for reduced virulence are provided in the following references, which also describe examples of mycovirus RNAs. Mycovirus RNAs have been identified in fungal isolates representing all major classes of fungi (Buck, K. W., 1985, Fungal virology—as overview, p. 2–84. CRC Press, Inc., Boca Raton, Fla.; Lemke, P. A. 1979, Viruses and plasmids in fungi, p. 653. Marcel Dekker, Inc., New York; Nuss, D. L. and Koltin, Y., 1990, Annu. Rev. Phytopathology, 28, 37–58). Examples of mycoviruses of this invention which reduce virulence in pathogenic fungi include mycovirus infected strains of the Dutch elm disease fungus, *Ophiostoma ulmi* (H. J. Rogers, K. W. Buck and C. M. Brasier, 1987, Nature, 329, 558–560), the peach canker fungus, *Leucostoma persoonii* (S. Hammer, D. W. Fulbright and G. C. Adams, 1989, Phytopathology, 79, 568–572), The potato pathogen, *Rhizoctonia solani* (Bandy, B. P. and S. M. Tavantzis, 1990, the general root rot pathogen, *Chalara elegans* (Bottacin, A. M., Levesque, C. A. and Punja, Z. K., 1993, Phytopathology, 83, 303–312 and the best characterized example, the chestnut blight fungus, *Cryphonectria parasitica* (Nuss, D. L., 1992, Microbiological Reviews; 56, 561–576; Choi, G. H. and Nuss, D. L. 1992, Science, 257, 800–803).

When fungus has been thus transfected with the coding strand of mycovirus RNA, this. RNA reduces the ability of the naturally virulent fungus to cause disease in plants. By means of this invention, virulent fungi pathogenic to plants which do not naturally contain mycovirus RNA may be transfected with mycovirus RNA and their virulence thereby reduced. Such virulent fungi which do not contain mycovirus RNA are known in the art and also may be determined by having no detectable mycovirus RNA by conventional isolation and detection methods. (Morris and Dodds, Phytopathology 69, 854–858 (1979).

An example of a mycovirus RNA is mycovirus RNA of the genus *Hypovirus*. Hypovirus RNA is preferred as the mycovirus RNA of this invention. An example of a hypovirus RNA is the hypovirus RNA which occurs naturally in the fungus *Cryphonectria parasitica*. A preferred hypovirus RNA is isolate CHV1-713 obtained from *C. parasitica* strain EP713. The sequence of this hypovirus RNA is provided in Shapira et al. EMBO J. 10, 731 (1991).

Preferred fungi of this invention are *Cryphonectria cubensis*, *Cryphonectria havanensis*, or *Endothia gyrosa* which have been transfected with CHV1-713 coding strand RNA transcript.

Also part of this invention is a composition which comprises a fungus, said fungus comprising a cell of a naturally virulent fungus causing disease in plants which cell is transfected with a coding strand of a mycovirus RNA which mycovirus RNA reduces the ability of said naturally virulent fungus to cause disease in plants and said mycovirus RNA being transmissible by said cell to other cells of the fungus, and a carrier nontoxic to plants, said fungus being present in said composition in sufficient amounts to treat fungal disease in plants when applied to a plant. The compositions of this invention may include one fungus or a collection of fungi. A preferred mycovirus RNA is hypovirus RNA.

Various formulations of the compositions are possible and are produced by conventional methods. Agronomically acceptable adjuvants and carriers are employable to disperse the fungi, spores, or active portions thereof. Precise formulations and dosages may be selected to best facilitate the spread of hypovirulence for a given application. For example, a paste consisting of equal parts fungal mycelia and sterilized bentonite or plugs of fungal mycelium grown on agar plates can be applied to mechanical wounds made around the margin of disease cankers. Alternatively, conidia (asexual spores) of hypovirulent fungal strains can be sprayed on infected trees at a concentration of approximately $5 \times 10^6$ per ml of water or other suitable liquid.

(Jaynes, R. A. and Elliston, J. E. (1980) Phytopathology, 70, 453–456; T. Turchetti and G. Maresi (1988) EPPO Bulletin, 18, 67–72).

The composition may be aqueous, a dust or powder, a wettable powder, an emulsion, a granular form a paste or any known type of formulation depending on how it is to be applied. As examples of means of application, a paste, in particular paste made up of fungal mycelia or hyphae with appropriate carriers and components as described below, could be applied directly to plants. Powders can be dispersed by air, and aqueous solutions sprayed. Another application method is to bore holes around the periphery of a canker of an infected plant, and insert into the holes mycelial paste as described above.

Compositions may include additives such as surfactants, nutrients, buffers, biological or chemical pesticides, and pentrating agents, in particular in the case of aqueous compositions. Included in particular in dry compositions are inert powders, stabilizing agents, salts, anticaking agents, nutrients, buffers, film-forming material.

Aqueous compositions may be aerosols, foliage sprays, mists, and other known compositions.

The compositions of this invention may include a collection of fungi, meaning fungi of more than one different species, all of which have reduced virulence according to this invention.

A sufficient amount of fungus for treatment is a level which provides for establishment of the fungus or spore cells on the treated plants and for their ability to multiply and transmit the hypovirus to infecting virulent fungi.

The compositions of this invention, when applied to a plant which is infected with a virulent fungus (by conventional methods and as described above) allow a fungus of this invention to reduce the virulence of the infection by itself displacing the virulent fungi, and in addition by transmitting mycovirus RNA to the infecting virulent fungi to reduce the virulence of the infecting fungus. Effectiveness of treatment can be determined by measuring a), rate of expansion of treated canker or lesion (Jaynes and Elliston, supra) or general condition of treated plants, eg., growth rate, ratio of living to dead plants, yield, biomass etc. (S. L. Anagnostakis (1990), Forest Science 36, 113–124). Therefore, sufficient amounts of fungus for treatment may be determined by these methods.

Accordingly, this invention also provides a method for treating fungal diseases in plants which comprises administering to a plant infected with a naturally virulent infecting fungus, the composition of this invention comprising a fungus which comprises a cell of a naturally virulent fungus causing disease in plants transfected with a coding strand of a mycovirus RNA which reduces the ability of the naturally virulent fungus to cause disease in plants, and being transmissible by said cell to cells of the fungus, and a suitable carrier nontoxic to plants. The composition is applied to a plant by known methods as described, and in an amount sufficient to treat said fungal disease caused by said infecting fungus, determined as described above.

For most effective treatment the fungus or fungi of this invention which are in the composition should be of the same species as the infecting virulent fungus or fungi. The species of the infecting fungus may be determined by known methods. A composition including a fungus of this invention which is of the same species as the infecting fungus may then be selected for the treatment. The composition may be produced by obtaining a cell of the infecting fungus and transfecting the cell with mycovirus in accordance with this invention, obtaining a fungus of this invention as described herein, then formulating the composition with the fungus, as also described.

A preferred mycovirus RNA is hypovirus RNA. This method is particularly useful where the composition comprises the fungus *Endothia gyrosa* of this invention, and the plant is an oak tree infected with *Endothia gyrosa*. This composition is also useful for eucalyptus trees infected with one or both of the fungi *Cryphonectria cubensis* and *Cryphonectria havanensis*, where the composition comprises one or both of the fungi *Cryphonectria cubensis* and *Cryphonectria havanensis* of this invention.

This invention also includes a method for preventing fungal diseases in plants which comprises administering to a plant the composition of this invention, in order to prevent infection by a fungal pathogen, where the composition is applied to the plant in an amount sufficient to prevent infection of said plant with a naturally virulent fungus. The specific fungus or fungi whose infection is prevented by this method will be those of the same species as the fungus or fungi in the composition.

This invention includes a method for reducing the virulence of a naturally virulent fungus causing disease in plants, which reduced virulence is transmissible to cells of said fungus. This method is performed by providing a cell of a naturally virulent fungus and transfecting the cell with the coding strand of a mycovirus RNA so as to incorporate said RNA into the cytoplasm of the cell, allowing replication of the mycovirus RNA in the cell. Incorporation of the mycovirus RNA confers reduced virulence on this cell, which is in turn transmissible to other cells of the fungus. Accordingly, the cell is allowed to transmit the mycovirus to other cells of the fungus. By this means a naturally virulent fungus whose virulence is reduced is obtained. This is a method by which the fungi of this invention may be produced.

Any naturally virulent fungus may be obtained as described above, for example from an infected plant, and cells of such a fungus are obtained by known methods. Mycovirus RNA is also obtained as described above. Specifically, mycovirus RNA may be isolated from a virulent fungus and inserted into a cell. In a preferred method, the cell walls are removed from the cells and the resulting spheroplasts are transfected with mycovirus RNA. A preferred mycovirus RNA is hypovirus RNA.

Any conventional method of transfecting a cell may be used, for example by means of a vector such as a suitable virus, plasmid, or any other construct which may be engineered to insert a virus or a part of a virus into a fungus or fungal cell. Alternatively, the mycovirus RNA may be transfected directly into the cell. A preferred method of transfection is electroporation, by methods known in the art and described in Example 1 below.

The mycovirus RNA may be transcribed from a cDNA strand. In a preferred method, the cDNA strand is a full-length copy of CHV1-713 hypovirus RNA obtained by known methods from *C. parasitica* (Shapira et al. EMBO J. 10, 731 (1991) and as described in Example 1. Alternatively, such a strand can be produced by known methods of nucleic acid synthesis from the sequence of CHV1-713.

The following examples are provided to illustrate the invention but are not intended to limit the invention in any manner.

METHODS

Example 1

Figure 1A:
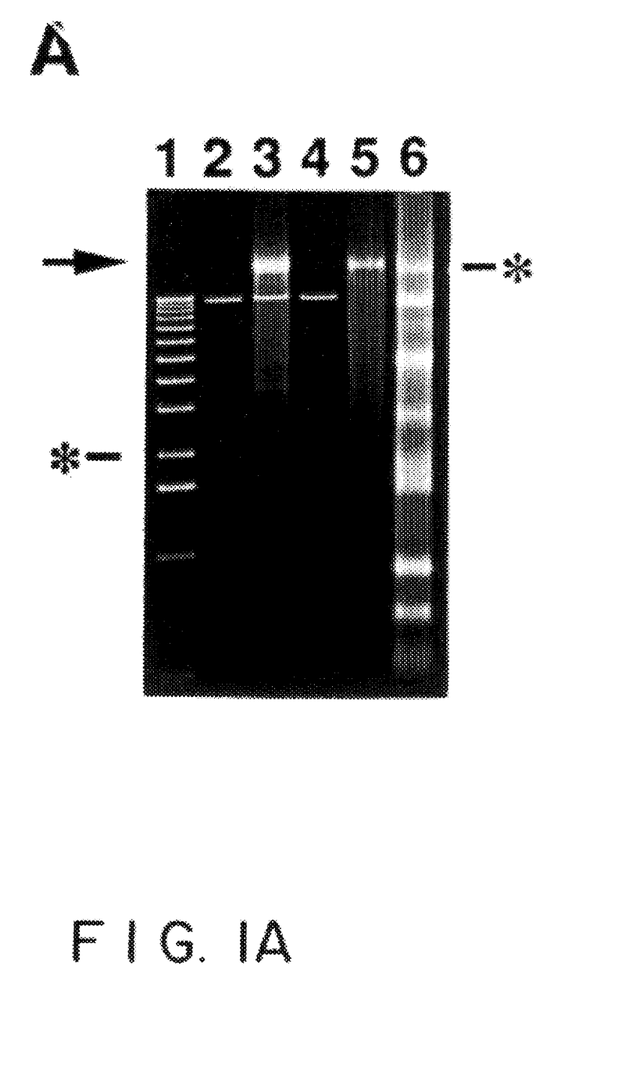
FIGS. 1A–1C. Cell-free synthesis of full-length hypovirus transcripts and their use to transfect *C. parasitica* spheroplasts. (A): Agarose gel analysis of T7-polymerase dependent cell-free transcription reactions with Spe I linearized pLDST. A full-length transcript of CHV1-713 hypovirus RNA coding strand was generated by cell-free transcription of Spe I linearized plasmid pLDST. Plasmid pLDST contains a full-length cDNA copy of CHV1-713 L-dsRNA (Shapira et al., EMBO J. 10, 731 (1991)) flanked at the 5'-terminus by a unique Ssp I restriction site and the bacteriophage T7 promoter sequence SEQ ID NO: 1 (TAATACGACTCACTATAG) and at the 3'-terminus by 22 adenosine residues, corresponding to the natural heterogeneous poly A tail found in L-dsRNA (Shapira et al., supra), followed by a unique Spe I restriction site, all inserted between the Xba I and Hind III sites of plasmid pUC19 [described in Choi and Nuss, Science, 257, 800 (1992)]. Lane 1, 1 Kbp DNA ladder (*, 2 Kbp); lane 6, ssRNA markers (*, 9.5 Kb). Lane 2, linearized pLDST; lane 3, complete transcription reaction; lane 4, complete transcription reaction treated with RNase; lane 5, complete transcription reaction treated with DNase. Arrow indicates the 12.7 Kb full-length viral transcript. (B): Agarose gel analysis of dsRNA recovered from transfected *C. parasitica* mycelia (Hillman, et al. *Phytopathology* 80, 950 (1990)). Lane 1, DNA marker (*, 2 Kbp); lane 2, dsRNA extracted from hypovirulent *C. parasitica* strain EP713; lane 3, dsRNA recovered from regenerated mycelia transfected with linearized pLDST template; lane 4, with a completed transcription reaction, and lane 5, with a transcription reaction that had been treated either with RNase or (lane 6) with DNase prior to transfection. L-dsRNA and residual ribosomal RNAs are indicated at the right (G. H. Choi, D. L. Nuss, *Science* 257, 800 (1992)). Comparable transfection results were obtained whether or not m$^7$G(5')ppp(5')G was added to the in vitro transcription reaction. Transfection with a modified synthetic transcript (introduced Not I site at L-dsRNA map position 12,038) yielded transfectants with the corresponding modified L-dsRNA as determined by combined reverse transcription and PCR (Choi and Nuss, supra). (C): Expansion of hypovirus host range with infectious synthetic viral transcripts. Lane 1, 1 Kb DNA ladder (*, 2 Kbp); lanes 2, dsRNA recovered from *C. parasitica* strain EP713; lanes 3–6, dsRNAs recovered from transfected *C. radicalis*, *C. havanensis* (ATCC 56124), *E. gyrosa* (ATCC 48192), and *C. cubensis* (ATCC 64159), respectively.

Transcripts corresponding to the viral RNA coding strand were synthesized from a full-length cDNA copy of CHV1-

Figure 1B:
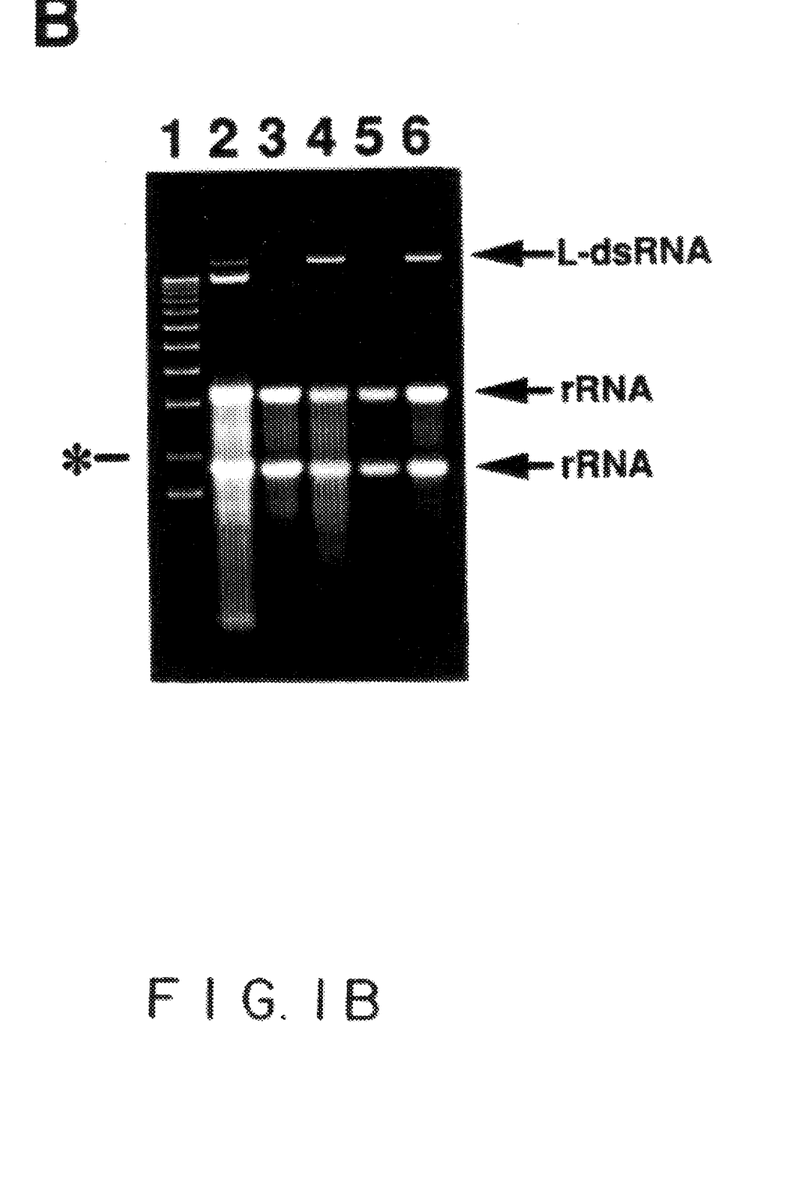

713 L-dsRNA in plasmid pLDST (FIG. 1A). Electroporation of spheroplasts derived from *C. parasitica* strain EP155, the same strain as the hypovirulent strain EP713 but lacking virus, with linearized pLDST DNA failed to yield virus-containing transfectants (FIG. 1B). In contrast, electroporation with a mixture of plasmid and viral transcript, or DNase-treated transcript, yielded mycelia that contained cytoplasmic replicating L-dsRNA (FIG. 1B). These results demonstrate that a synthetic transcript corresponding to the coding strand of a mycovirus dsRNA can initiate an infection when introduced into fungal spheroplasts.

Plasmid pLDST used as template for cell-free synthesis of the vital coding strand transcript contained a full-length cDNA copy of CHV1-713 L-dsRNA (Choi, supra) flanked at the 5'-terminus by a bacteriophage T7 promoter sequence SEQ ID NO: 1 (TAATACGACTCACTATAG) and at the 3'-terminus by 22 adenosine residues, corresponding to the natural heterogenous poly (A) tail found in L-dsRNA (Shapira, et al. supra), followed by a unique SpeI restriction site. Thus, the synthetic transcript generated from Spe I linearized pLDST contained a non-vital G residue at the 5'-terminus and 22 adenosine residues followed by the vector sequence CUAG at the 3'-terminus. Cell-free transcription was performed with Riboprobe transcription reagents (Promega) according to the manufacturer's instructions. Where indicated, reactions were treated with 3 units RQ1-DNase or 0.3 units RNase A for 20 min at 37 C. All reactions were extracted with phenol/chloroform and nucleic acids were recovered by ethanol precipitation. Fungal spheroplasts ($2 \times 10^7$/ml) (Churchill, et al. Curt. Genet. 17, 25 (1991)) in 100 ml of 1M sorbitol were transfected with nucleic acid preparations (in 20 ml $H_2O$ containing 200 U RNasin) by electroporation at 1.5 kv, 200 W and 25 mF. The spheroplast suspensions were diluted with 750 ml ice cold 1M sorbitol and incubated on ice for 5–10 min. Two hundred ml aliquots were then placed in the center of 10 cm petri dishes, surrounded by 20 ml of regeneration medium (Churchill, et al., supra), gently mixed and incubated at 25 C. Mycelial plugs were transferred from the edge of the regenerated colony to potato dextrose agar. Since hyphal strands regenerated from spheroplasts fuse with neighboring strands, replicating hypovirus RNA from transfected spheroplast is able to spread throughout the colony. Consequently, virus-infected mycelia can be readily obtained even at low transfection efficiencies without the need for a selectable marker.

Example 2

Figure 1C:
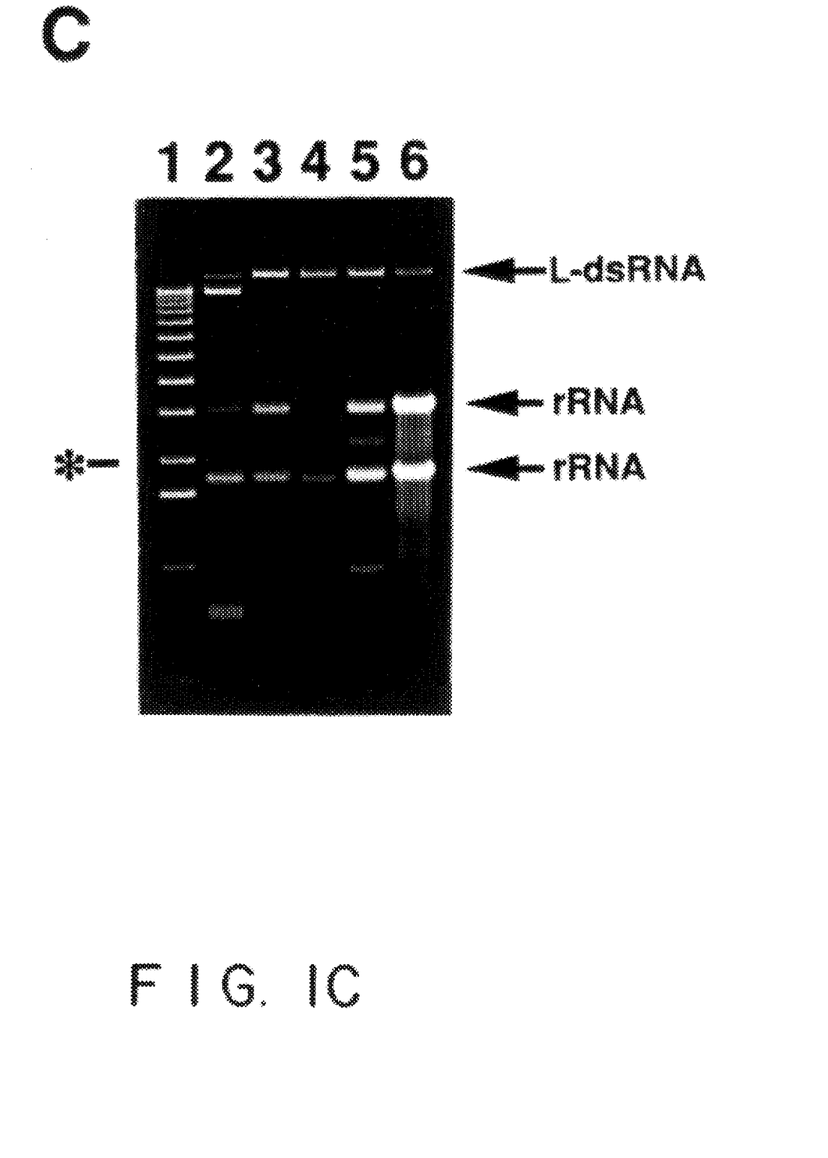
Figure 2A:
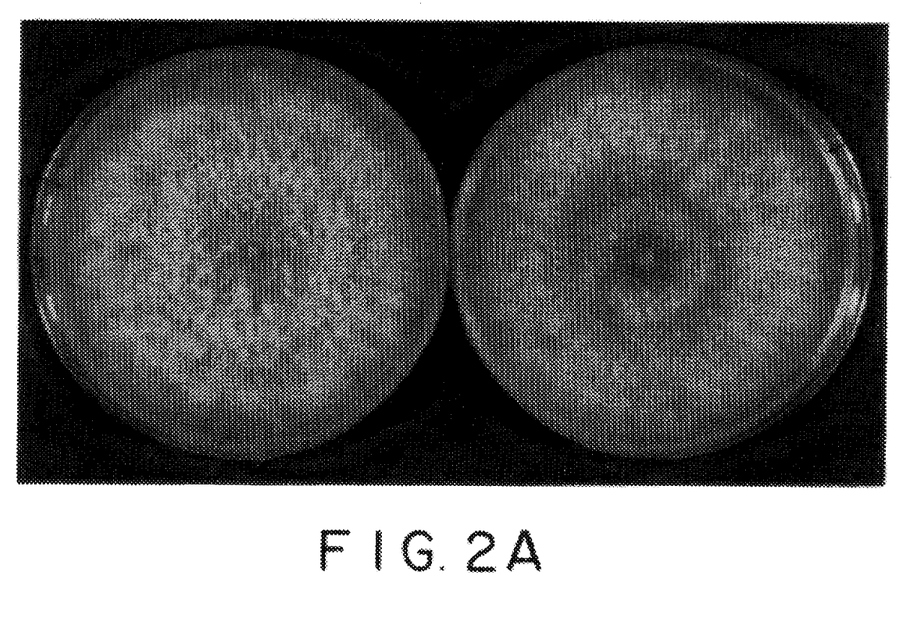
FIGS. 2A–2D. Morphological changes associated with replication of hypovirus RNA in transfected fungal species. Each pair compares the morphology of virus free- (left) and mycovirus transfected-colonies (right) on potato dextrose agar media. Morphological changes observed for *C. radicalis* (A) were similar to those observed for engineered hypovirulent *C. parasitica* strains (Choi and Nuss, supra), including a slight reduction in growth rate, suppression of orange pigmentation and reduced sporulation. Infection of *E. gyrosa* (B) and *C. cubensis* (C), resulted in more severe phenotypic changes, including reduction in growth rate and increased production of a dark brown and a bright orange pigment, respectively. Infection of *C. havanensis* (D), resulted in mild morphological changes.
Figure 2B:
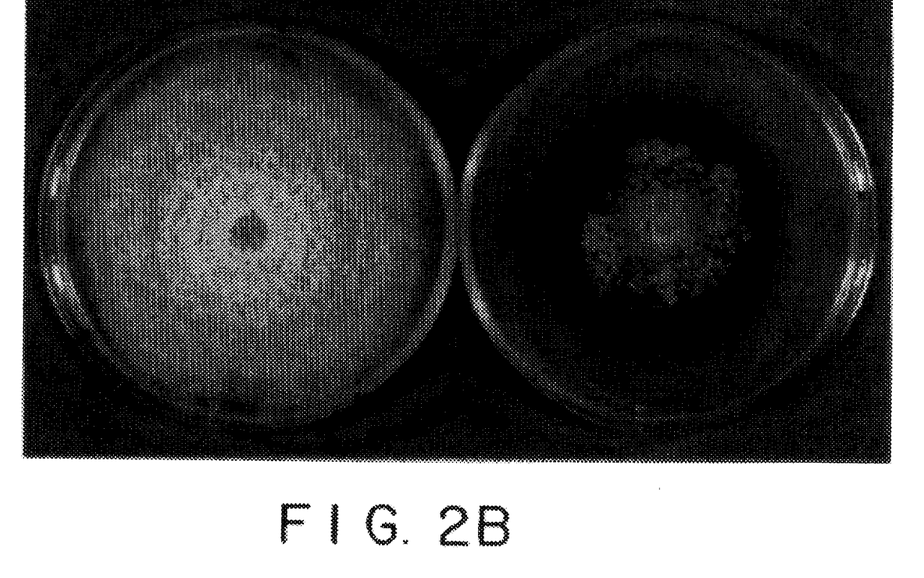
Figure 2C:
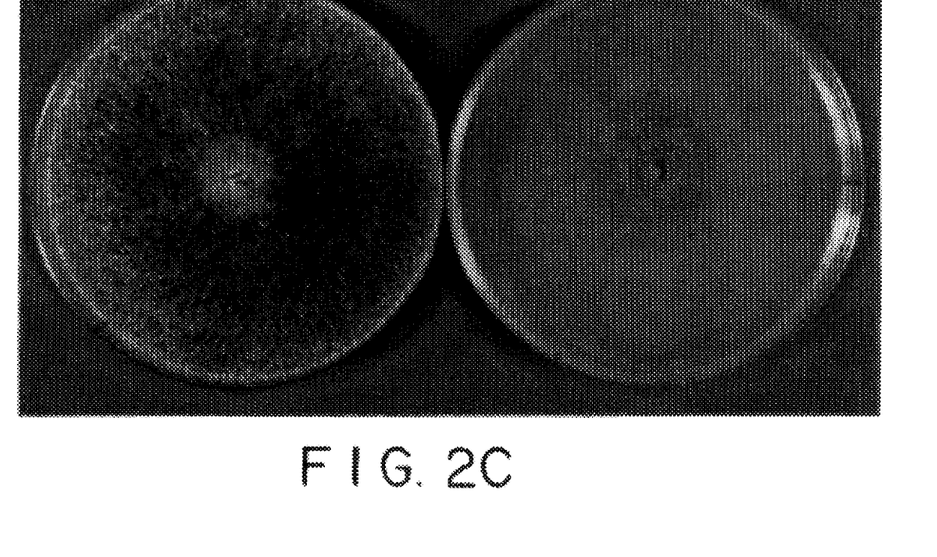
Figure 2D:
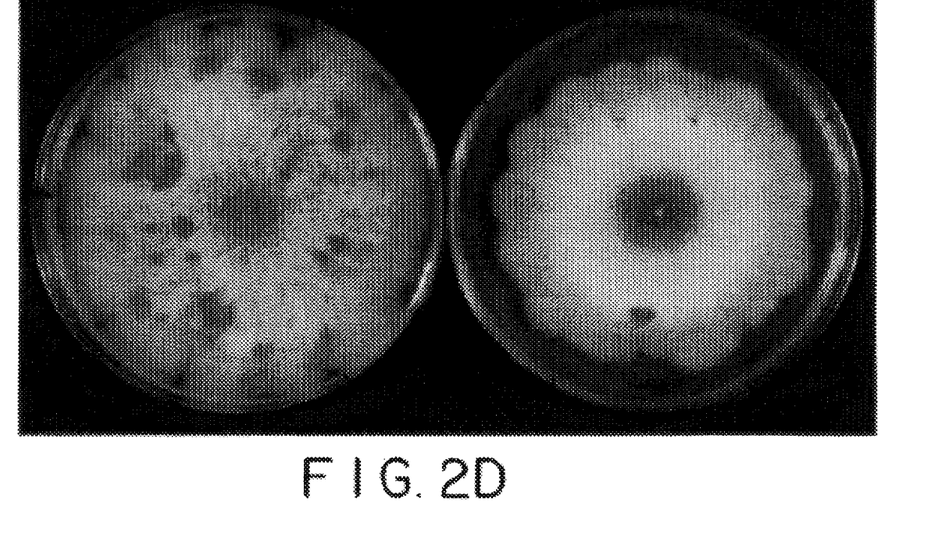

Three members of the genus *Cryphonectria* (family Valsaceae) and one member of a separate taxonomic family (Gnomoniaceae) in the genus *Endothia* (M. E. Barr, *The Diaporthales in North America* (J. Cramer, Lehre, Germany, 1978), J. A. Micales, R. J. Stipes, *Mycologia Mem.* XXVI, 99 (1986) and M. K. Roane, et al. in *Chestnut Blight, Other Endothia Diseases and the Genus Endothia* (APS Press, St Paul, Minn., 1986), pp. 1–53) were transfected. The fungi tested were *C. cubensis* (Bruner) Hodges, causal agent of a canker disease of *Eucalyptus* spp. in many tropical areas of the world. (C. S. Hodges, *Myocologia* 72, 542 (1980)). *C. havanensis* (Bruner) Barr, also a pathogen of *Eucalyptus*, Roane supra, *C. radicalis* (Schw. ex Fries) Barr, a nonpathogenic saprophytic species (Roane, supra) and *E. gyrosa* (Schw. ex Fries) a canker pathogen of *Quercus* spp., mainly pin oak (D. N. Appel, R. J. Stipes, *Plant Dis.* 68, 851 (1984)). These species do not harbor natural hypoviruses, and hypovirus dsRNA was not transmissible from *C. parasitica* to these species by anastomosis. All five hypovirus transfected fungal species were found to efficiently convert virus-free strains of the same species following anastomosis as described (Choi, supra). No cytoplasmic virus transmission was observed from transfected *C. parasitica* to other fungal species and vice versa. Each of these fungal species supported hypovirus replication following transfection with the infectious CHV1-713 L-dsRNA transcript (FIG. 1 C).

Hypoviruses cause a variety of profound phenotypic changes in the natural host *C. parasitica* (S. L. Anagnostakis, *Science* 215, 466 (1982), Hillman, supra, G. H. Choi, D. L. Nuss, EMBO J. 11, 473 (1992) and Craven, et al. *J. Virol.* 67, 6513 (1993)). Hypovirus infection of additional fungal species was also accompanied by a variety of morphological changes (FIG. 2), as well as attenuation of fungal virulence (Table 1). Therefore, these morphological changes indicate reduced virulence and may be used as additional assays for reduced virulence. The expansion of hypovirus-mediated virulence attenuation to *E. gyrosa*, classified as a member of a separate taxonomic family, (Barr, supra), demonstrates that virus-mediated hypovirulence will find broader application in addition to biological control of chestnut blight.

Example 3

Figure 3:
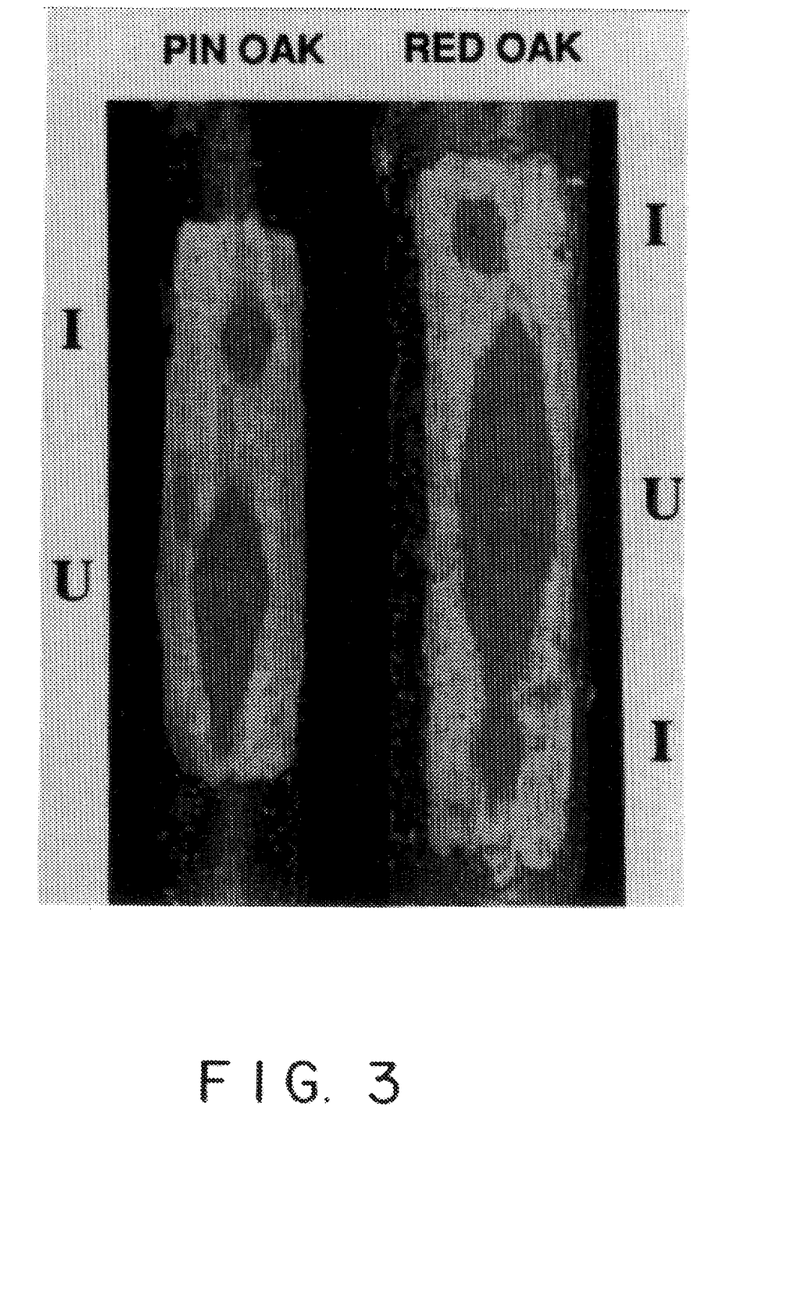

Virulence assays were performed for untransfected and hypovirus-transfected *E. gyrosa* on dormant pin oak and red oak stems as described (R. A. Jaynes, J. E. Elliston, *Phytopathology* 70, 453 (1980)). Thirty-five days after inoculation, bark was removed around lesions and the extent of the necrotic tissue was measured. Data are presented as mean lesion area (square centimeter) based on four inoculations each of untransfected *E. gyrosa* and hypovirus-transfected *E. gyrosa* per stem (FIG. 3; Table 1). Differences between lesion formation by virus-free and virus-containing fungal strains were highly significant for both host tree stems as indicated by the t-values listed. *E. gyrosa* was chosen for the virulence assay because the natural plant hosts were readily available, it is a serious pathogen of stressed pin oak in urban settings (Barr, supra) and it is classified in a different taxonomic family than members of the genus *Cryphonectria*. (Appel and Stipes, supra)

TABLE I

Virulence Assay of Unifected and Hypovirus-Infected *E. gyrosa* Mean Canker Area ($cm^2$)

| Stem Number | Pin Oak | | Red Oak | |
| --- | --- | --- | --- | --- |
| | Transfected *E. gyrosa* | Hypovirus-transfected *E. gyrosa* | Untransfected *E. gyrosa* | Hypovirus-transfected *E. gyros* |
| 1 | 6.89 | 0.60 | 22.28 | 2.96 |
| 2 | 6.01 | 0.94 | 19.82 | 2.81 |
| 3 | 5.67 | 0.55 | 24.92 | 2.47 |
| 4 | 7.94 | 0.84 | 20.43 | 2.01 |
| 5 | 4.58 | 0.61 | 26.33 | 2.40 |
| Mean | 6.22 ± 1.27 | 0.71 ± 0.17 | 22.76 ± 2.82 | 2.53 ± 0.37 |
| t-value | 10.18 | | 15.70 | |
| Probability | <0.0005 | | <0.0005 | |

We claim:

1. A method for artificially inserting into a fungal cell a selected mycovirus RNA, which method comprises obtaining the coding strand of said mycovirus RNA, and causing said coding strand to enter said fungal cell by performing electroporation.

2. A method of claim 1 wherein the mycovirus RNA is CHV1-713 RNA and the fungal cell is an *Endothia gyrosa* cell.

* * * * *